United States Patent [19]

Mesens et al.

[11] 4,213,963
[45] Jul. 22, 1980

[54] FLUSPIRILENE-CONTAINING COMPOSITIONS

[75] Inventors: Jean Mesens, Geel; Victor Haagen, Vosselaar, both of Belgium

[73] Assignee: Janssen Pharmaceutica N.V., Beerse, Belgium

[21] Appl. No.: 969,526

[22] Filed: Dec. 14, 1978

[51] Int. Cl.$^2$ ............................................. A61K 31/79
[52] U.S. Cl. ...................................................... 424/80
[58] Field of Search ......................................... 424/80

[56] References Cited

U.S. PATENT DOCUMENTS

| | | | |
|---|---|---|---|
| 3,105,007 | 9/1963 | Bodkin | 424/80 |
| 3,351,527 | 11/1967 | Apat et al. | 424/80 |
| 3,557,280 | 1/1971 | Weber et al. | 424/80 |
| 3,634,586 | 1/1972 | Kaser et al. | 424/80 |
| 3,674,859 | 7/1972 | Beutel et al. | 424/80 |
| 3,763,142 | 10/1973 | Manning | 424/80 |
| 3,787,410 | 1/1974 | Anderson et al. | 424/80 |
| 3,891,750 | 6/1975 | Hess et al. | 424/80 |

*Primary Examiner*—Stanley J. Friedman
*Attorney, Agent, or Firm*—Geoffrey G. Dellenbaugh

[57] ABSTRACT

Improved fluspirilene-containing compositions for intramuscular administration and a method of preparing the same.

2 Claims, No Drawings

FLUSPIRILENE-CONTAINING COMPOSITIONS

DESCRIPTION OF THE INVENTION

This invention relates to novel fluspirilene-containing compositions, suitable for intramuscular administration, and to a method of preparing such compositions.

Fluspirilene, being chemically designated as 8-[4,4-bis(4-fluorophenyl)butyl]-1-phenyl-1,3,8-triazaspiro[4,5]decan-4-one, belongs to the class of 1,3,8-triazaspiro[4,5]decan-4-ones which are described in U.S. Pat. No. 3,238,216.

It is a long-acting neuroleptic, the pharmacological behaviour of which is outlined in Arzneim. Forsch. (Drug Research), 20, 1689 (1970).

Fluspirilene is only slightly soluble in neutral or weakly alkaline aqueous medium (solubility<0.01 g/100 ml water). Consequently the drug is administered to patients in the form of an aqueous suspension of microcrystalline product.

It is evident that, in view of the particular, i.e. intramuscular, way of administration, such microcrystalline suspensions have to meet certain strict criteria in order to be fully acceptable to the patient to be treated. Suspensions for intramuscular administration may not be irritating nor cause any tissue damage at the site of injection. The pH of the suspension should therefore be almost neutral and the suspension should contain virtually no particles of a diameter greater than about $30\mu$. However, in order to maintain a uniform blood-level of the drug over a longer period of time the particle size distribution is even more critical since the rate of dissolution of the drug and consequently of its uptake in the patients blood is dependent on the specific surface of the suspended particles and hence on the particle size. When the particles are too small the uptake of the drug may be too quick resulting in a temporary overdosing of the patient which may occassionally cause extrapyramidal effects. It has been found that in a preferred embodiment at least 50% of the particles should have a diameter between $3\mu$ and $10\mu$, and at least 70% a diameter between $2\mu$ and $15\mu$.

Fluspirilene-containing compositions which are used at present comprise a suspension of fluspirilene at a concentration of 2 mg/ml in an aqueous medium which further contains per milliliter 12 mg of benzenemethanol, 5 mg of polyvinylpyrrolidone, a tensioactive agent and about 0.08 mmoles of phosphate buffer consisting of sodium mono- and dihydrogen phosphate in such proportion as to bring the pH of the medium at a value of from about 7.1 to about 7.4.

Although such existing compositions were found quite acceptable they are however not completely free of disadvantages. It has indeed come to light that said existing compositions when stored for a rather long period show a certain tendency to cake. Consequently resuspension may in these cases by achieved only by vigorous agitation during a sufficiently long time. Otherwise the eventual presence of unbroken lumps would prevent intramuscular injection of the composition.

Cake-formation will be more pronounced when the fluspirilene-content of the composition is high, for example 10 mg/ml. Due to the increased thickness of the layer of precipitated product, gravitational forces will obviously have more impact and cake-formation will be stimulated considerably.

By the present invention there is provided a fluspirilene-containing composition which is suitable for intramuscular administration to a patient in need of same and which is completely free of the above-mentioned disadvantages.

More particularly, the present invention provides fluspirilene-containing compositions which, in comparison with existing compositions contain significantly higher concentrations of polyvinylpyrrolidone and phosphate buffer. As a result of this property of the medium there are obtained flocculated suspensions which are easily resuspended even after standing for long periods.

The compositions according to the present invention show thus a clear superiority over the previously known non-flocculated, fluspirilene-containing compositions.

By the present invention there are provided fluspirilene-containing compositions which comprise per milliliter (i) from 1.5 to 15 mg of microcrystalline fluspirilene preferably having such a particle size distribution that not less than 50% of the particles have a sphere diameter of from $3\mu$ to $10\mu$ and not less than 70% of the particles have a sphere diameter of from $2\mu$ to $15\mu$;

(ii) from 8 to 40 mg of water-soluble polyvinylpyrrolidone; and (iii) from 0.13 to 0.42 mmoles of phosphate buffer, adjusting the pH of the composition to a value between 6.0 and 8.2 and preferably between 6.7 and 7.5.

Of the different types of polyvinylpyrrolidone, having different molecular weights those are suitable which are sufficiently soluble in aqueous medium and which do not raise the viscosity of the medium above the upper limit for a convenient intramuscular injection. Polyvinylpyrrolidone polymers having an average molecular weight of from about 10.000 to about 40.000 are satisfactory for the purpose of the present invention. The phosphate buffer usually comprises a mixture of sodium mono- and dihydrogen phosphate. In addition to the constituents listed above the composition will normally comprise other substances and/or solvents which facilitate the preparation of the composition and which do not adversely affect the stability and the efficacy of the composition nor its ability of being administered by intramuscular injection. In view of the particular process by which the composition is prepared it will normally comprise a physiologically acceptable organic solvent, e.g. benzenemethanol and an also physiologically acceptable tensio-active agent, preferably a polyoxyethylene polymer such as, for example, polysorbate 80.

In fact, the compositions according to the present invention can generally be prepared by the following process. A concentrated solution of fluspirilene in a mixture of an appropriate, physiologically acceptable, organic solvent, e.g. benzenemethanol and an appropriate, physiologically acceptable surfactant, e.g. polysorbate 80, is added slowly while vigorous stirring to an aqueous medium containing from 2 to 6 mg/ml of polyvinylpyrrolidone. In order to obtain an effectively controled precipitation the mixing is performed by feeding the concentrated fluspirilene solution and the aqueous medium to a homogenizer at a constant flow rate. The microsuspension which is obtained is allowed to settle and optionally part of the supernatant phase is removed. The portion of the supernatant phase which is eventually removed is dependent on the desired concentration of fluspirilene in the ultimate composition. Indeed, when increasing the concentration of fluspirilene, there is introduced more benzenemethanol and surfactant. By decanting the suspension part of the solvent and surfactant is removed. Thereafter there is added to the mixture an aqueous solution comprising polyvinylpyrrolidone and phosphate buffer in such concentration as to bring the concentration of these constituents in the final composition at the required value.

As a result of the elevated concentration of polyvinylpyrrolidone and phosphate buffer in the medium the suspended microcrystalline fluspirilene particles form aggregates with polyvinylpyrrolidone which are sedimenting much easier than the above-described separate particles. As a result there is obtained a voluminous sediment which is easily resuspended by minimal agitation.

The invention is further illustrated by the following example which by no way is limiting the scope thereof.

EXAMPLE I

A. Preparation of Solutions (i) Solution 1

40 g of fluspirilene are dissolved in 240 g of benzenemethanol at 60°–70° C. Then there are added 200 g of polysorbate 80 and the mixture is kept at 60°–70° C. The solution is filtered sterile using a membrane filter.

(ii) Solution 2

87 g of anhydrous disodium hydrogenphosphate, 28 g of sodium dihydrogenphosphate dihydrate and 50 g of polyvinylpyrrolidone are dissolved in about 8 liter of pyrogen-free water. After completion there is further added pyrogen-free water till a volume of 9.560 liter. The solution is sterilized by membrane-filtration.

(iii) Solution 3

114.6 g of anhydric disodium hydrogenphosphate, 36.8 g of sodium dihydrogen phosphate dihydrate and 30 g of polyvinylpyrrolidone are dissolved in about 1.8 liter of pyrogen-free water. After completion pyrogen-free water is added till a volume of 2 liter and the solution is sterilized by membrane-filtration.

B. Preparation of Microcrystalline Suspension

Solution 2, stored in a 20 liter-vessel is pumped at constant flow rate into a 2 liter-precipitation vessel fitted with a homogenizer and having an overflow to the 20 liter-vessel. At the same time solution 1, stored in a 2 liter-flask at 80°–90° C. is fed at constant flow rate into the precipitation vessel. After completion of the procedure there is obtained a microcrystalline suspension having such a particle size distribution that about 88% of the particles have diameters between $3\mu$ and $10\mu$ and 98% between $2\mu$ and $15\mu$. Particles of diameter size greater than $30\mu$ are virtually absent.

C. Stabilization of the Microsuspension

The microsuspension, obtained by the foregoing procedure is allowed to stand for 24 hours. 8 liter of the clear supernatant solution are decanted and subsequently solution 3 is added while stirring. The suspension is filled sterile into 1 ml ampoules.

The composition thus obtained is suitable for intramuscular administration to a patient in need of same.

What we claim is:

1. An aqueous fluspirilene-containing pharmaceutical composition for intramuscular administration which comprises per milliliter of composition from 1.5 to 15 mg of microcrystalline fluspirilene having such a particle size distribution that not less than 50% of the particles have a sphere diameter between $3\mu$ and $10\mu$ and not less than 70% of the particles have a sphere diameter between $2\mu$ and $15\mu$; from 8 to 40 mg of water-soluble polyvinylpyrrolidone; and from 0.13 to 0.42 millimoles of phosphate buffer, adjusting the pH of the composition to a value between 6.0 and 8.2.

2. A pharmaceutical composition according to claim 1 wherein said polyvinylpyrrolidone has an average molecular weight of from 10,000 to 40,000.

* * * * *